(12) United States Patent
Akutsu et al.

(10) Patent No.: US 6,422,747 B2
(45) Date of Patent: Jul. 23, 2002

(54) MOVABLE TYPE X-RAY PHOTOGRAPHING APPARATUS

(75) Inventors: Koji Akutsu, Nara; Tatsuya Araki, Ohmihachiman, both of (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/778,924

(22) Filed: Feb. 8, 2001

(30) Foreign Application Priority Data

Mar. 22, 2000 (JP) .................................. 2000-080381

(51) Int. Cl.$^7$ .................................................. H05G 1/02
(52) U.S. Cl. ..................... 378/198; 180/19.3; 180/19.1; 378/193
(58) Field of Search ........................ 378/198, 193; 180/19.1, 19.3; 318/2, 14

(56) References Cited

U.S. PATENT DOCUMENTS

| | | | |
|---|---|---|---|
| 4,167,983 A | * 9/1979 | Seider et al. | 180/19.1 |
| 4,319,171 A | * 3/1982 | Motoori | 318/293 |
| 4,646,862 A | * 3/1987 | Meili | 180/19.3 |
| 5,351,282 A | * 9/1994 | Kadowaki et al. | 378/193 |
| 5,657,828 A | * 8/1997 | Nagamachi | 180/168 |
| 5,927,414 A | * 7/1999 | Kan et al. | 180/19.3 |
| 6,193,415 B1 | * 2/2001 | Kadowaki et al. | 378/197 |

* cited by examiner

Primary Examiner—Robert H. Kim
Assistant Examiner—George Wang
(74) Attorney, Agent, or Firm—Kanesaka & Takeuchi

(57) ABSTRACT

In a movable type X-ray photographing apparatus, when a lever handle is operated, a force F for pushing the lever handle is inputted into a CPU from right and left pressure sensors provided in the handle. The CPU receives signals of rotational numbers V of motors from right and left encoders, and calculates a pulse width $W=\alpha \times f(V) \times F$. In accordance with the calculated pulse width W, a PWM control circuit carries out an ON-OFF duty control of a switching element in a bridge circuit of a motor driving circuit. An output torque T of the motor driving circuit is subjected to a PWM control so as to maintain a relationship $(T=\alpha \times f)$. Accordingly, the torque T truly proportional to the pushing force F is outputted from the motor, and a natural operation can be achieved.

6 Claims, 3 Drawing Sheets

MOVABLE TYPE X-RAY PHOTOGRAPHING APPARATUS

BACKGROUND OF THE INVENTION AND RELATED ART STATEMENT

The present invention relates to an X-ray photographing apparatus of a power driving type which moves forwardly or backwardly in response to a force of an operation handle. More particularly, the present invention relates to a movable type X-ray photographing apparatus, which includes bridge circuits for driving formed of switching elements; driving motors, each being positioned at a center of the bridge circuit; and pulse width control circuits for controlling ON-OFF duty of torque of the motors by the bridge circuits.

FIGS. 2(a) through 2(c) show a movable type conventional X-ray photographing apparatus. FIG. 2(a) shows a front view of the movable type conventional X-ray photographing apparatus; FIG. 2(b) shows a side view; and FIG. 2(c) shows a plan view. This apparatus is formed of an X-ray tube 18; an arm 19 for supporting the X-ray tube 18; a column 20 which is rotatable on a truck or base 21; an ascending and descending section in which the arm 19 moves vertically or up and down along the column 20; and freely rotatable or pivotable front wheels 23 and rear wheels 22 (right wheel 2 and left wheel 1) which are incapable of steering. The truck 21 is provided with an X-ray control section, and moves forwardly or backwardly by means of driving motors (a right motor 6 and a left motor 5) provided at a lower section when a lever handle 14 disposed in a handle supporting base 17 attached to the truck 21 is operated forwardly or rearwardly.

The arm 19, which includes a supporting mechanism for the X-ray tube 18 and a rotational mechanism therefor and extends or retracts horizontally, moves smoothly vertically along the column 20, so as to be balanced. A collimator (X-ray radiation port) of the X-ray tube 18 is directed to any directions and spatial positions in accordance with a photographing portion of a subject, that is, a person to be examined.

Since the weight of the movable type X-ray photographing apparatus may become more than 450 kg, it is very difficult to move the truck or base without help of the power. In general, a rear portion of the truck 21 is provided with a pair of rear wheels 22, which are attached not to be steered, and a front portion of the truck 21 is supported by a pair of casters. That is, front wheels 23 are freely rotatable or can be turned. The rear wheels 22 are generally driven by the driving motors (the right motor 6 and the left motor 5) mounted in the truck.

The truck 21 includes an internal power supply formed of an automobile battery and an inverter with a main circuit of 100–120 V and 60 Hz, and the truck 21 also includes a high-voltage transformer and a condenser. In many cases, there is used an apparatus of a one-touch system, wherein a control circuit thereof is solid-systematized and a photographing operation is automatically programmed.

Also, rubber tires or the like are used in the truck 21, so that the apparatus can freely enter or leave a patient's room, an operating room, or an elevator, and the truck 21 also includes a brake system, a cassette box, and accessories.

It is important that the movably type X-ray photographing apparatus is small, light-weight, and excellent in a moving operation ability as a mobile type apparatus. Also, the X-ray photographing apparatus is easily moved to a bedroom, a technician room, an operating room, a children room or a pediatric room, an X-ray room, an infant room or the like in a hospital, and conveniently used for an X-ray photographing or radiography at a job site, that is, the location where the apparatus is moved.

FIG. 3 shows a control block diagram of the movable type X-ray photographing apparatus. A left wheel 1 and a right wheel 2 shown in an upper section in FIG. 3 are respectively driven by the left motor 5 and the right motor 6, and the left motor 5 and the right motor 6 are individually controlled by a motor driving circuit 9 through a left output 7 and a right output 8. The motor driving circuit 9 is subjected to a switching control by pulse width modulation (PWM) by means of a PWM control circuit 10. A duty control width of the switching control is controlled by a signal from a CPU (central processing unit) 35. When an operator operates the lever handle 14 of the truck 21 forwardly or rearwardly, signals from a left pressure sensor 15 and a right pressure sensor 16 disposed at both ends of the lever handle 14 are individually inputted to the CPU 35 as a left input 12 (left Ft) and a right input 13 (right Ft).

On the other hand, from a left encoder 3 and a right encoder 4, which are respectively provided at axles of the left wheel 1 and the right wheel 2 and detect rotational speeds, signals of a rotational speed Vt at left and a rotational speed Vt at right are inputted to the CPU 35. Then, the CPU 35 controls the PWM control circuit 10 with PWM control width which is proportional to the input signals Ft of the forward or backward movement from the left pressure sensor 15 and the right pressure sensor 16. Accordingly, the motor driving circuit 9 is actuated, and the left motor 5 and the right motor 6 are rotated at output torque T. The rotational speeds Vt of the motors are detected by the left encoder 3 and right encoder 4, and the speed signals Vt are inputted to the CPU 35.

If the rotational speeds Vt are lower than a predetermined rotational frequency or number corresponding to the input signals Ft, the PWM control width is enlarged, and if the rotational speeds Vt are higher than the aforementioned predetermined rotational frequency or number, the PWM control width is narrowed. The rotational speeds are fed back and controlled. The CPU 35 inputs the duty control width signal corresponding to the PWM control width into the PWM control circuit 10; the PWM control circuit 10 controls the motor driving circuit 9; and the motor driving circuit 9 controls the rotational speeds V of the left motor 5 and the right motor 6.

The lever handle 14 is connected to the truck 21 through spring members which are relatively rigid but flexible. The spring members connected to both sides of the truck 21 are formed of hard plate springs, and by providing these spring members, the position of the lever handle 14 can be changed slightly in the front and rear directions in response to the force applied to the lever handle 14, such as a force for pushing or pulling the lever handle 14.

At both ends of the lever handle 14, a pair of linear magnets moving together with the lever handle 14 is respectively attached. On the other hand, a pair of Hall-effect sensors (the left pressure sensor 15 and the right pressure sensor 16) is attached to the truck 21, and disposed respectively adjacent to the corresponding magnets. The Hall-effect sensors are respectively connected to power supplies (not shown). When the Hall-effect sensor (left pressure sensor 15 or right pressure sensor 16) is located at the center positions with respect to the magnet, an output signal of the Hall-effect sensor (left pressure sensor 15 or right pressure sensor 16) become zero level. When the magnet is moved or displaced, the output signal of the Hall-effect sensor (left pressure sensor 15 or right pressure sensor 16) changes approximately linearly between the positive maximum value and the negative maximum value. The code of the sensor signal, that is, polarity, shows the direction of the displacement of the lever handle 14, and the magnitude of the sensor signal is proportional to the amount of the displacement.

By operating the lever handle 14 forwardly and rearwardly, the lever handle 14 can be relatively easily displaced by the spring action of the spring members, and at the same time, when the lever handle 14 is released, the lever handle 14 can be quickly returned to a neutral position or a center position.

The conventional X-ray photographing apparatus is structured as described above, and it has a mechanism that both ends of the lever handle 14 are supported by the plate springs as the spring members. While the plate springs support a load in a direction of gravity, the lever handle 14 is returned to the neutral position when the operational force is zero. Also, for the detection of the operational force, there is used a method in which a position of the magnet attached to the lever handle 14 is detected by the Hall-effect sensor. Also, there can be used a method in which a strain gauge is bonded to the plate spring supporting the lever handle 14. Further, in response to the force Ft for pushing the lever handle 14, the signal of the rotational frequency Vt is received, so that the duty width of the PWM control circuit 10 is fed back and controlled.

However, in case of suddenly changing the operation, the apparatus acts unnaturally, and can not be operated well. Also, in the direct current (DC) motors (right motor 6 and left motor 5), even if the PWM control circuit 10 carries out the same duty (proportions of ON and OFF are the same) control, there is caused a phenomena that the output torque T is decreased in inversely proportional to the rotational frequency Vt. In the method that the force Ft for pushing the lever handle 14 is amplified and outputted from the motors (right motor 6 and left motor 5), even though the lever handle 14 is pushed by the same force Ft, there is caused a phenomena that the output torque T is reduced as the speed increases. Thus, it is difficult to achieve the comfortable and natural operation.

In particular, in case of driving the heavy-weight apparatus, such as the movably type X-ray photographing apparatus, the motors (right motor 6 and left motor 5) having the large torque T are adopted. Thus, when the motors (right motor 6 and left motor 5) are controlled at the amplification rate such that enough torque T can be obtained even at high speed, the motors provide torque T, which is more than required at low speed, resulting in extremely lowering the operation feeling. Also, if the amplification rate is reduced in order to improve the operation ability at the low speed, a high-speed movement of the apparatus can not be maintained without continuously applying the strong or big force to the lever handle 14, resulting in that the apparatus is not suitable for a practical use.

Accordingly, the present invention has been made in view of the foregoing, and an object of the invention is to provide a movable type X-ray photographing apparatus, which can be operated with a natural operation when an operator pushes the lever handle.

Further objects and advantages of the invention will be apparent from the following description of the invention.

SUMMARY OF THE INVENTION

To achieve the aforementioned object, the present invention provides a movable type X-ray photographing apparatus, which comprises an operation handle attached to a moving device or base of an X-ray photographing apparatus; a plurality of pressure sensors individually disposed at right and left, and front and rear portions of the handle to be pressed in response to an operation force applied to both ends of the handle in a forward direction to thereby detect the operation force and issue signals thereof; a pair of wheels individually driven; a pair of motors disposed at axles of the wheels for driving the wheels; bridge circuits for driving including switching elements, each motor being electrically located at a center of the bridge circuit; pulse width control circuits for controlling ON-OFF duty of torques of the motors by the bridge circuits; a pair of encoders for detecting rotational speeds of the driven wheels and issuing signals of the rotational speeds; and a central processing unit (CPU) controlling the torques of the motors in accordance with the signals from the pressure sensors and the signals from the encoders to rotate the wheels for moving the X-ray photographing apparatus. The CPU controls a pulse width of the pulse width control circuit proportional to a value calculated by a formula, that is, {(a maximum value of a pulse control width)/(a maximum output torque of the motor)}×{(a maximum rotational number of the motor)/(the maximum rotational number of the motor–a rotational number of the motor)}×(a force for pushing the operation handle).

The X-ray photographing apparatus of the invention is structured as described above, and upon receiving the input signal F for pushing the operation handle and the input signal of the rotational frequency V of the motor, the CPU calculates the formula: {(the maximum value of the pulse control width)/(the maximum output torque of the motor) }×{(the maximum rotational number of the motor)/(the maximum rotational number of the motor –the rotational number V of the motor)}×(the force F for pushing the operation handle), to thereby control the pulse width W of the PWM control in the pulse width control circuit. Then, the switching element of the motor driving circuit is turned ON-OFF with the duty of the pulse width W, to thereby rotate the direct current motor. Accordingly, since the aforementioned calculation is carried out while maintaining the relationship expressed by a formula: an output torque T of the motor =(amplification factor $\alpha$) ×(the pushing force F), the apparatus can be operated with a natural operation touch when the operator pushes the operation handle.

DETAILED DESCRIPTION OF PREFERRED EMBODIMENTS

Figure 1:
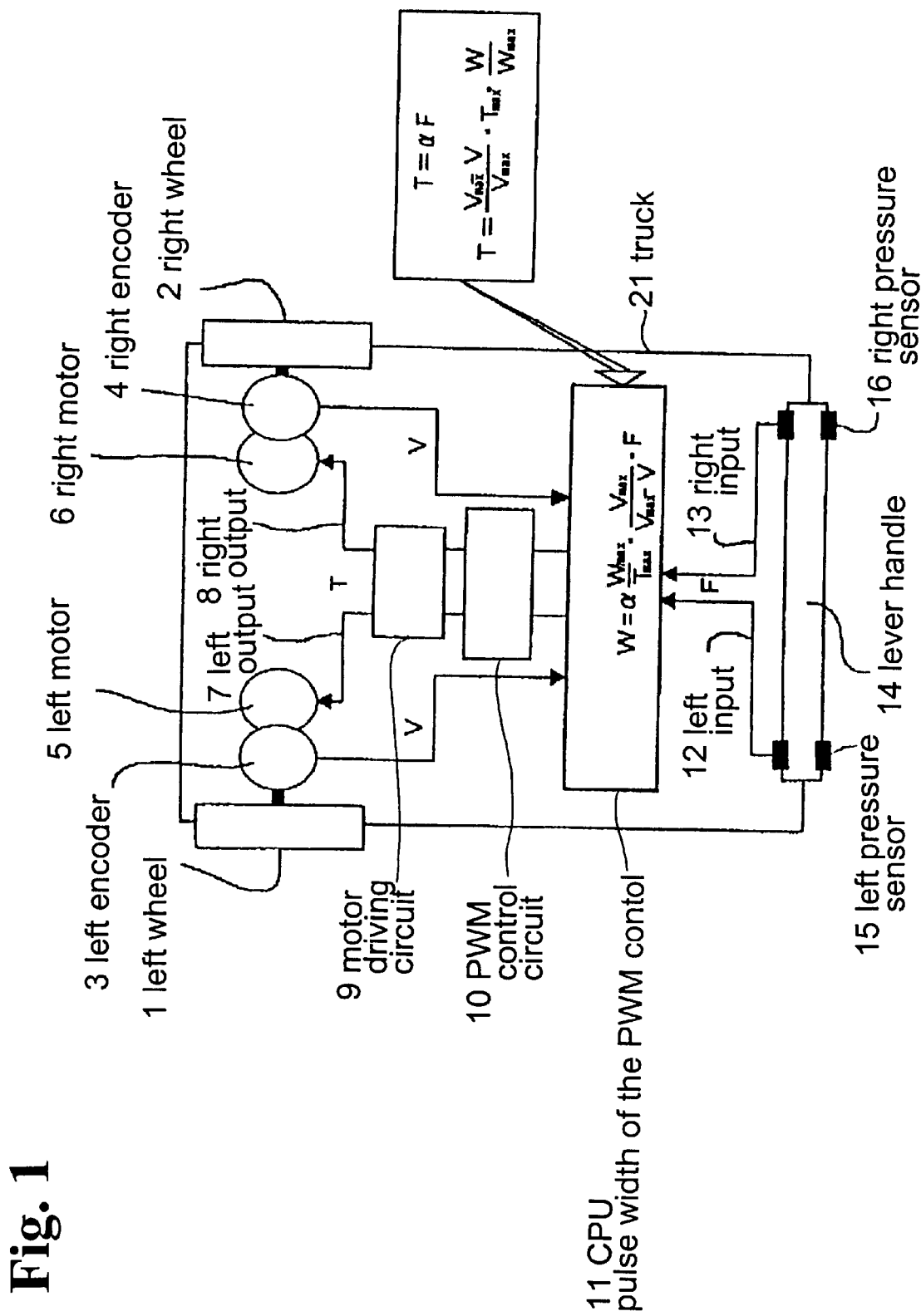
FIG. 1 is an explanatory diagram showing an embodiment of a movable type X-ray photographing apparatus of the invention.
Figures 2A, 2B, 2C:
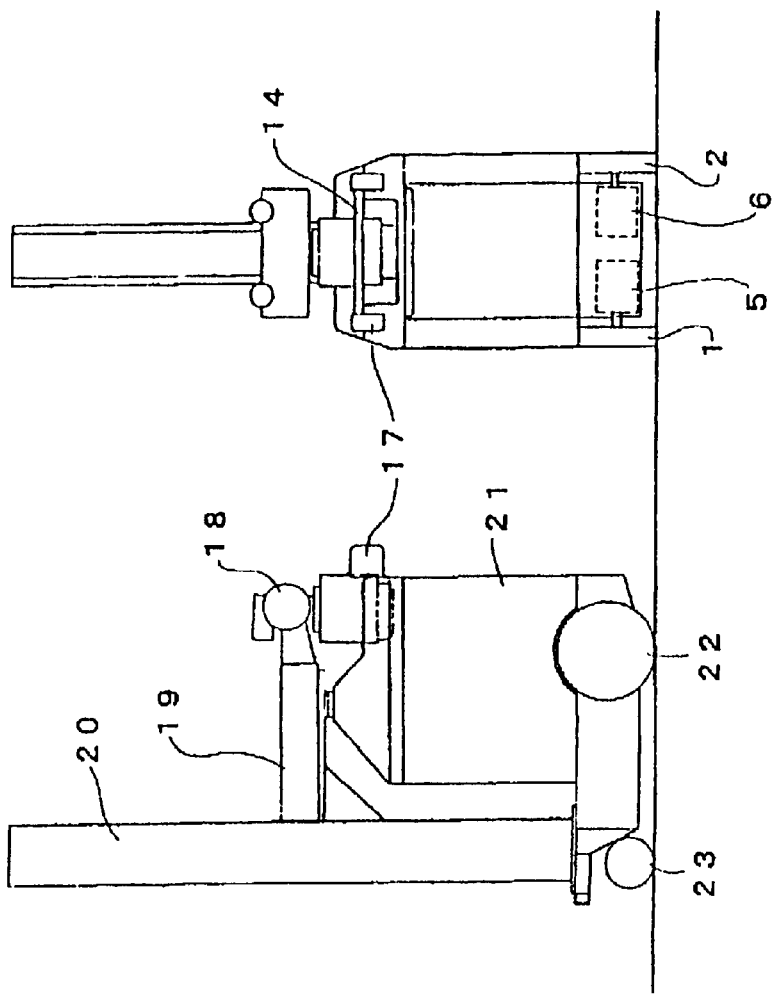
FIGS. 2(*a*) through 2(*c*) are explanatory views showing an appearance of a conventional movable type X-ray photographing apparatus, wherein FIG. 2(*a*) shows a front view, FIG. 2(*b*) shows a side view, and FIG. 2(*c*) shows a plan view.

An embodiment of the movable type X-ray photographing apparatus of the invention will be explained with reference to FIG. 1. FIG. 1 is a diagram showing a control block circuit of the movable type X-ray photographing apparatus of the invention. The X-ray photographing apparatus of the invention is formed of a lever handle 14 which is provided with sensors (left pressure sensors 15 and right pressure sensors 16) at left front, left rear, right front and right rear thereof, and outputs a force F (left input 12 and right input 13) pushed by an operator; a CPU 11 which controls the pulse width of a pulse width modulation control circuit 10 by calculating a formula: {(a maximum value of a pulse control width)/(a maximum output torque of a motor)}×{(a maximum rotational number of the motor)/(the maximum rotational number of the motor −rotational number V of the motor)}×(a force F for pushing the operation handle 14), in response to the signals of the pushing force F and signals of the rotational number or frequency V from encoders (a left encoder 3 and a right encoder 4); a PWM control circuit 10 which carries out a duty control of a motor driving circuit 9 by changing the pulse width in response to the signal from the CPU 11; the motor driving circuit 9 provided with bridge circuits for driving the motors and having switching elements, in which one motor (a left motor 5 or a right motor 6) is electrically disposed at a center of one bridge circuit; the motors (the left motor 5 and the right motor 6) which drive right and left wheels (a right wheel 2 and a left wheel 1); the encoders (the left encoder 3 and the right encoder 4) which detect the rotational number or frequency of the wheels (the left wheel 1 and the right wheel 2); left and right wheels (the left wheel 1 and the right wheel 2); and a truck or base 21.

Figure 3:
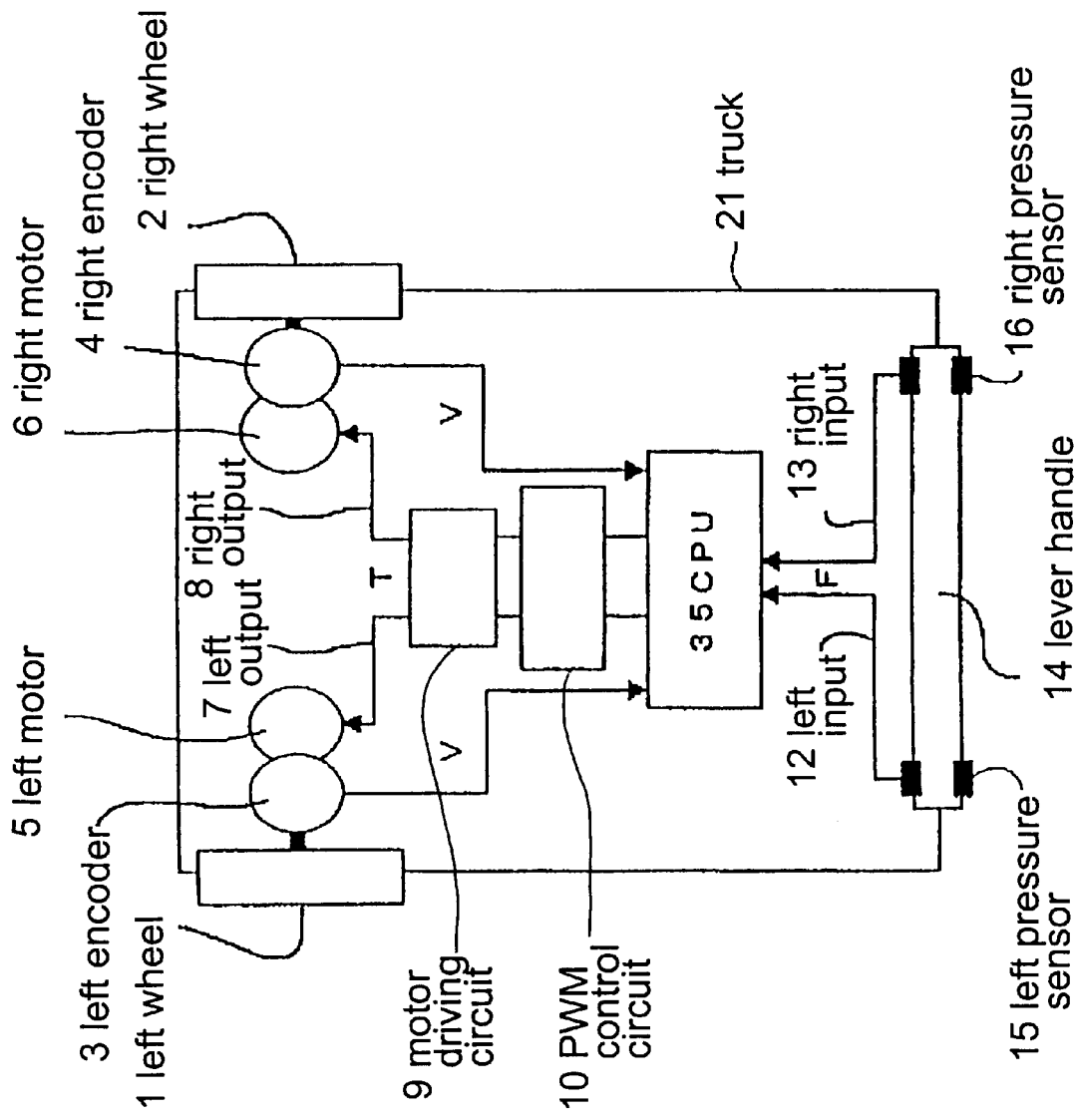
FIG. 3 is an explanatory diagram showing a control block circuit of the conventional movable type X-ray photographing apparatus.

In the movable type X-ray photographing apparatus of the invention, as compared with the conventional apparatus shown in FIG. 3, the CPU 11 in the apparatus of the invention is different from the conventional CPU 35. The conventional CPU 35 controls the PWM control circuit 10 at a PWM control width which is proportional to the input signals F of the forward or backward movement from the sensors (the left pressure sensors 15 and the right pressure sensors 16), and the motors (the left motor 5 and the right motor 6) are rotated at the output torque T through a left output 7 and a right output 8. Then, the encoders (the left encoder 3 and the right encoder 4) detect the rotational speeds V of the motors, and the rotational speeds V are inputted to the CPU 35. In the CPU 35, if the rotational speed V is lower than the predetermined rotational number corresponding to the input signal Ft, the PWM control width is widened; and if the rotational speed V is higher than the predetermined rotational number corresponding to the input signal Ft, the PWM control width is reduced. The rotational speed is fed back and controlled.

On the other hand, the CPU 11 in the apparatus of the present invention receives input signals F of the forward or backward movement from the sensors (the left pressure sensors 15 and the right pressure sensors 16) and the signals of the rotational numbers from the encoders (the left encoder 3 and the right encoder 4), and calculates the following formula (3), that is, (amplification factor)× {(a maximum value of the pulse control width)/(a maximum output torque of the motor)}×{(the maximum rotational number of the motor)/(the maximum rotational number of the motor−rotational number V of the motor)}×(the force F of pushing the operation handle). Then, the pulse width of the PWM control circuit 10 is controlled at the calculated pulse width, and ON-OFF control of the switching element of the bridge circuit in the motor driving circuit 9 is carried out at the duty proportional to the control amount, so that the direct current motor (the right motor 6 or the left motor 5) is rotated.

$$T=(V_{max}-V)/V_{max} \times T_{max} \times W/W_{max} \qquad \text{formula (1)}$$

T: output torque
V: rotational number
W: PWM control width
max: maximum value $$T=\alpha F \qquad \text{formula (2)}$$

F: force for pushing the handle
α: amplification rate $$W=\alpha \times W_{max}/T_{max} \times V_{max}/(V_{max}-V) \times F \qquad \text{formula (3)}$$

The CPU 11 receives the inputs of the force F for pushing the lever handle 14 and the rotational number or speed V of the motor, and in accordance with the formula (3) which is derived from the logical formula (1) and the formula (2), the PWM control width W is outputted to the PWM control circuit 10.

The relationship between the output torque T in the DC motor (the right motor 6 or the left motor 5) and the rotational speed V is expressed by the formula (1). Namely, the output torque. T={(the maximum rotational number of the motor−the rotational number V of the motor)/(the maximum rotational number of the motor) }× (the maximum output torque of the motor)×{(the PWM control width)/(the maximum value of the pulse control width)}. Here, T shows the output torque of the motor; V shows the rotational number of the motor; W shows the PWM control width; and max shows each maximum value.

The relationship between the force F for pushing the lever handle 14 and the output torque T of the motor is expressed by the formula (2). Here, α shows an amplification rate.

Therefore, from the formula (1) and the formula (2), the formula (3) for the PWM control width W is derived. Namely, the PWM control width W equals to (amplification rate)× {(the maximum value of the pulse control width)/(the maximum output torque of the motor)}×{(the maximum rotational number of the motor)/(the maximum rotational number of the motor−the rotational number V of the motor) }× (the force F for pushing the operation handle).

Therefore, with respect to the pushing force F, the PWM control width W is controlled as a function of the rotational number V by the formula, that is, W=α×f (V)×F. Then, the output torque of the motor is outputted as T=k ($V_{max}$−V)× W=α×F. Thus, the torque T truly proportional to the pushing force F becomes the motor output, and the natural operation can be achieved.

The CPU 11 controls the PWM control circuit 10 at the PWM control width W calculated by the formula (3). Accordingly, even if the motor having the amplification rate a which can provide enough torque T at high speed is used and controlled, the torque T more than necessary does not occur by reducing the pushing force F at a low speed, resulting in improving the operation ability at a low speed. Therefore, without applying the strong or large force to the lever handle 14, the high-speed movement can be maintained. Then, even if the lever handle 14 is pushed by the same force both at a high speed and at a low speed, the output torque T is not reduced as the speed increases. Thus, a comfortable and natural operation touch can be achieved.

The movable type X-ray photographing apparatus of the invention is structured as described above, and when the operator pushes the lever handle, the pulse width control signal W, which is outputted to the PWM control circuit with respect to the pushing force F from the pressure sensors disposed at both ends of the lever handle, is controlled by the formula, that is, W=α×f (V) ×F, and the output torque of the motor is outputted as T=k ($V_{max}$−V)×W=αx F. Thus, the torque T truly proportional to the pushing force F is outputted from the motor, so that the natural operation can be achieved.

Also, since the maximum rotational frequency $V_{max}$ of the motor and the amplification rate α are used as parameters, even if the motors with different characteristics are connected, the apparatus can respond quickly.

Further, the feeling of heavy/light at the time of operation is expressed by the amplification factor α, and the balance of the operation ability at a low speed and a high speed is expressed by the maximum rotational frequency $V_{max}$, so that the apparatus can easily respond to a demand for further improving the operation ability.

While the invention has been explained with reference to the specific embodiments of the invention, the explanation is illustrative and the invention is limited only by the appended claims.

What is claimed is:

1. An X-ray photographing apparatus, comprising:
   a base for an X-ray photographing apparatus,
   an operation handle attached to the base,
   pressure sensors attached to the operation handle to be pressed by operation forces applied to the handle to thereby provide signals of the operation forces,
   a pair of driving wheels attached to the base to be driven individually,
   a pair of motors attached to the respective driving wheels for driving the wheels,
   bridge circuits electrically connected to the respective motors for driving the motors, each bridge circuit having a switching element and being arranged such that one of the motors is electrically placed at a center thereof,
   pulse width control circuits connected to the bridge circuits for controlling ON-OFF duty of torques of the respective motors,
   a pair of encoders for detecting rotational speeds of the wheels and issuing signals of the rotational speeds, and
   a central processing unit electrically connected to the bridge circuits and the pulse width control circuits for controlling the torques of the motors in accordance with the signal from the pressure sensors and the signals from the encoders to rotate the wheels for moving the X-ray photographing apparatus, said central processing unit controlling pulse width of the pulse width control circuit in proportion to a value calculated by a formula:

{(a maximum value of a pulse control width)/(a maximum output torque of the motor)}×{(a maximum rotational number of the motor)/(the maximum rotational number of the motor−a rotational number of the motor)}×(a force for pushing the operation handle).

2. An X-ray photographing apparatus according to claim 1, wherein the pressure sensors are individually disposed at right front, right rear, left front and left rear portions of the handle.

3. An X-ray photographing apparatus according to claim 1, wherein the torque of the motor is proportional to the pushing force of the handle.

4. An X-ray photographing apparatus according to claim 3, wherein the motor connected to one driving wheel is controlled by one driving circuit with one pulse width control circuit in response to the pressure sensor at one side of the operation handle.

5. An X-ray photographing apparatus according to claim 1, wherein said central processing unit controls the pulse width control circuits to provide the torques of the motors proportional to the force for pushing the operation handle.

6. An X-ray photographing apparatus according to claim 5, wherein the motors are controlled such that the torques of the motors are not reduced as rotational speeds of the motors increase.

* * * * *